(12) United States Patent
Ruth et al.

(10) Patent No.: US 7,755,767 B2
(45) Date of Patent: Jul. 13, 2010

(54) RESONATOR-AMPLIFIED ABSORPTION SPECTROMETER

(76) Inventors: Albert A. Ruth, 48 Nuns Walk, Ballyphehane, Cork (IE); Sven E. Fiedler, Ebersstrasse 70, 10827 Berlin (DE)

( * ) Notice: Subject to any disclaimer, the term of this patent is extended or adjusted under 35 U.S.C. 154(b) by 544 days.

(21) Appl. No.: 10/536,342

(22) PCT Filed: Nov. 24, 2003

(86) PCT No.: PCT/EP03/13174

§ 371 (c)(1),
(2), (4) Date: Jul. 11, 2005

(87) PCT Pub. No.: WO2004/048907

PCT Pub. Date: Jun. 10, 2004

(65) Prior Publication Data

US 2006/0072117 A1    Apr. 6, 2006

(30) Foreign Application Priority Data

Nov. 25, 2002    (DE) .............................. 102 55 022

(51) Int. Cl.
*G01B 9/02* (2006.01)
(52) U.S. Cl. ..................................... 356/454; 356/519
(58) Field of Classification Search ................ 356/454, 356/519
See application file for complete search history.

(56) References Cited

U.S. PATENT DOCUMENTS

| | | | |
|---|---|---|---|
| 3,524,066 A | | 8/1970 | Blakkan |
| 5,528,040 A | * | 6/1996 | Lehmann ................. 250/343 |
| 5,734,165 A | | 3/1998 | Unal et al. |
| 5,986,768 A | * | 11/1999 | Pipino ..................... 356/440 |
| 6,094,267 A | * | 7/2000 | Levenson et al. ........... 356/484 |
| 6,839,140 B1 | | 1/2005 | O'Keefe et al. |
| 7,012,696 B2 | * | 3/2006 | Orr et al. ................. 356/454 |

FOREIGN PATENT DOCUMENTS

EP    1 022 558 A3    1/2000

OTHER PUBLICATIONS

"Very Long Paths in Air" by J.U. White in J. Opt. Soc. Am. 66, 411, dated 1976.
"Cavity Enhanced Absorption and Cavity Enhanced Magnetic Rotation Spectroscopy" by R. Engeln, G. Berden, R. Peeters, and G. Meijer in Rev. Sci. Instr. 69, 3763, dated 1998.

(Continued)

*Primary Examiner*—Hwa S. A Lee
(74) *Attorney, Agent, or Firm*—Karl F. Milde, Jr.; Eckert Seamans Cherin & Mellott, LLC

(57) ABSTRACT

The invention relates to a device (10) for determining absorption of a sample, comprising an incoherent radiation source (12) for generating a measuring light beam (20), a resonator that is provided with at least two mirrors (30, 32) into which the measuring light beam can be coupled, a sample volume (38) for receiving an absorbing sample within the resonator (14), and a detector (18) for absorbing the radiation that can be decoupled from the resonator (14). The inventive device (10) includes spectrometric or interferometric means (16), provided between the radiation source (12) and the detector (18), for spectrally splitting the measuring light beam. Means may also be provided for generating a signal that represents the amplitude of the measuring light beam independently of the phase.

16 Claims, 3 Drawing Sheets

OTHER PUBLICATIONS

"A Fourier Transform Cavity Ring Down Spectrometer" by R. Engel and G. Meijer in Rev. Sci. Instr. 67, 2708, dated 1996.

"Pulse-Stacked Cavity Ring-Down Spectroscopy" by E.R. Crosson, P. Haar, G.A. Marcus, H.A. Schweitmann, B.A. Paldus, T.G. Spence, and N.R. Zare in Rev. Sci. Inst. 70, 4, 1999.

"Integrated Cavity Output Analysis of Ultra-Weak Absorption" by A. O'Keefe in Chem. Phys. Lett. 293 (1988), p. 331.

"Fourier Transform Phase Shift Cavity Ring Down Spectroscopy" by E. Hamers, D. Schramm, and R. Engeln in Chem. Phys. Lett. 365 (2002), pp. 237-243.

"Incoherent Broad-band Cavity-Enhanced Absorption Spectroscopy", S. Fiedler et al., Chemical Physics Letters 371 (2003) 284-294.

* cited by examiner

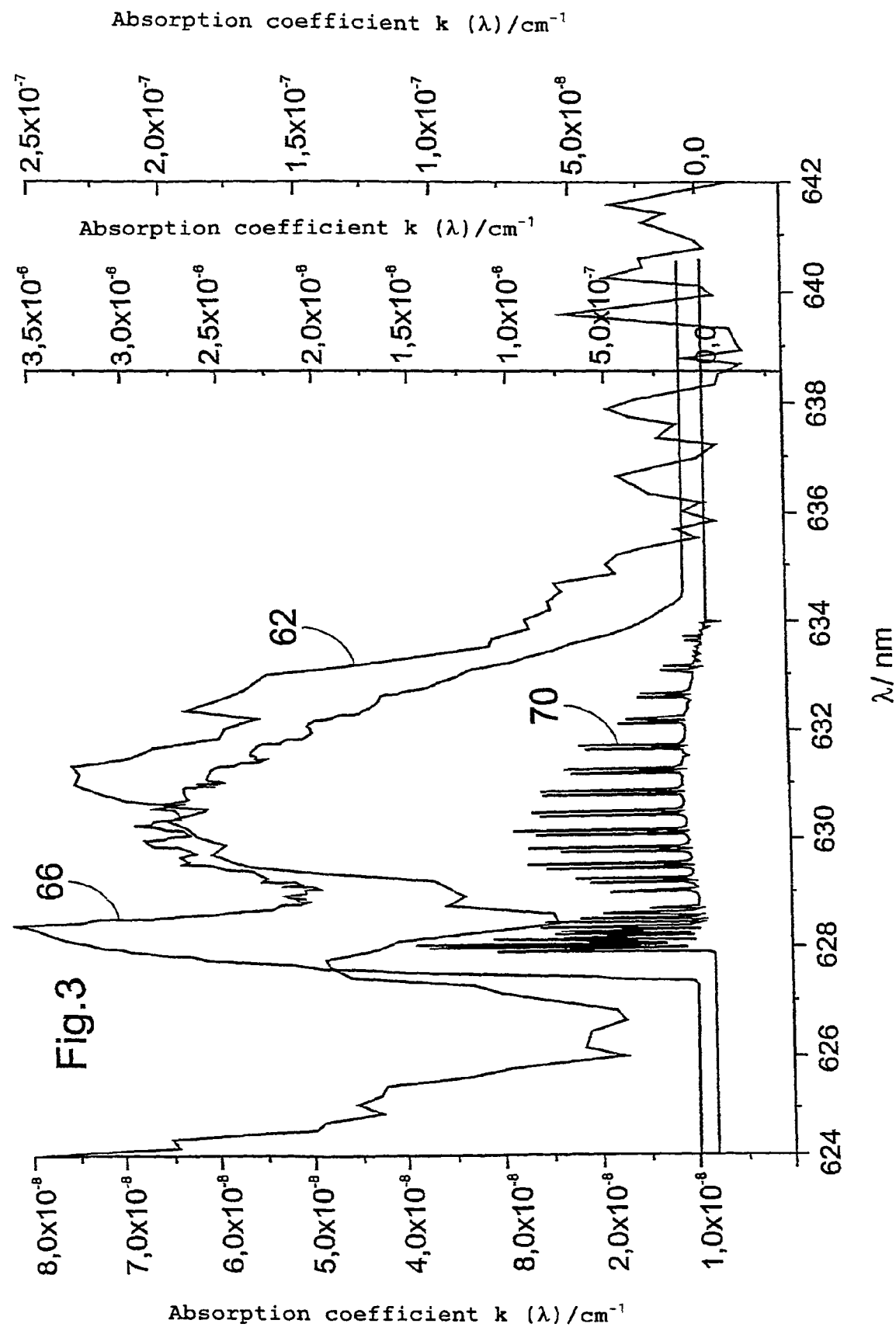

RESONATOR-AMPLIFIED ABSORPTION SPECTROMETER

BACKGROUND OF THE INVENTION

1. Technical Field

The invention relates to a device to determine the absorption in a sample that includes:
- a) An incoherent emission source to create a measuring light beam;
- b) A resonator with at least two mirrors to which the measurement light beam may be coupled as input;
- c) A sample volume to receive an absorbing sample within the resonator; and
- d) A detector to receive the beam that may be coupled to the output from the resonator.

The invention further relates to a method to operate such a device.

2. State of the Art

A method to measure the wavelength-dependent absorption of a material is known from classical absorption spectroscopy. In such a method, the sample is penetrated with white light. White light (continuum irradiation) consists of a so-called wavelength continuum, i.e., in the wavelength spectrum under consideration, irradiation occurs at all wavelengths. Contrastingly, monochromatic light is understood to be irradiation that is limited to a very narrow wavelength range, i.e., to consist of only one 'color.' In classical absorption spectroscopy, the light is split into varying wavelengths behind the sample by means of a monochromator. The resulting spectrum may be received using horizontal or surface detectors at the output of the monochromator. The sample does not absorb equally at all wavelengths. The absorption spectrum of the sample may be determined by measuring the irradiation with and without the sample, or with the help of a reference beam that passes through a reference medium without absorption. The molecules present in the sample may be identified based on the received absorption spectrum, e.g. by comparison with known molecular spectra. Further, the quantity of the molecules present in the sample may be determined. This is done by determination of the absorption coefficients that are dependent on the concentration and the wavelength-dependent extinction of the substance being observed. This known method is simple and low-cost, but provides very low sensitivity.

A method to measure atmospheric trace gasses is known as "DOAS" (Differential Optical Absorption Spectroscopy). In this method, the white light from a lamp is directed through the atmosphere for a distance of a few meters to several kilometers. A reflector reflects the irradiation toward a telescope, and the spectrum is received by a monochromator and a horizontal detector. When very long absorption paths are used, very low concentrations of trace gases may be determined. The disadvantages are low spatial resolution, long integration times at the detector, and the dimensions of the measuring facility. This makes the method expensive and inflexible.

For example, multiple-path cells (so-called multi-pass cells—MPAS) are known from the publication "Very long paths in air" by J. U. White in J. Opt. Soc. Am. 66, 411, of 1976. In them, continuum irradiation is guided through the sample using mirrors whereby the absorption path length is increased. This achieves an improved level of sensitivity. MPAS still suffers, however, from deficient sensitivity and unfavorable signal-to-noise ratio because of the loss at each mirror reflection. Further, there are problems in the practical realization of numerous transfixing paths. Because of the normally strong divergence from incoherent light sources, only a few transfixing paths are possible. Even if lasers are used, the number of transfixing paths is limited to about 100. The systems are also mechanically susceptible to inaccuracy because even the slightest de-adjustment of the mirrors causes a large alteration to the irradiation path.

Methods using lasers as coherent, monochromatic emission sources are known as Cavity Ring-Down Spectroscopy (CRDS) and Cavity Enhanced Absorption Spectroscopy (CEAS). In both methods, the laser light is coupled to the input of an optical resonator. A resonator consists of at least two mirrors with high reflectivity. These are particularly known in laser technology. The coupled light reflects within the resonator, and forms so-called modes at the resonator wavelength, i.e., standing waves of minima and maxima. The modes are not formed at other wavelengths.

The simplest resonator consists of two parallel planar/concave mirrors whose reflective surfaces face each other. There are also ring resonators consisting of several mirrors. At one of the resonator mirrors, light is decoupled out of the resonator and directed to a detector for measurement, where the measurement signal is created.

In the CRDS method, an absorbing sample is placed into the resonator. A laser pulse from a pulsed laser beam is coupled into the resonator. Because of reflection losses and losses upon output, the laser pulse light reflected, or stored, within the resonator becomes weaker, and the signal received at the detector is reduced. The temporal signal progression follows an exponential function with decay time $\tau_0$ if the sample does not absorb. Additional light losses occur within the resonator in the presence of an additional absorption by the sample at this wavelength. The decay time then decreases to a lesser value $\tau < \tau_0$. The absorption coefficient, and thus the sample quantity, may be determined from the decay time. This method requires reception and evaluation of a correspondingly temporally highly resolved signal by the detector. Further, a laser pulse with corresponding high intensity must be created in order to be capable of being registered at the detector, and to create a favorable signal-to-noise ratio.

The decay curve of the laser pulse intensity must be reproducible. Correspondingly high demands are placed on the individual components, which make the method more expensive. It is particularly disadvantageous that the absorption coefficient is measured only at one wavelength. In order to be able to measure at, other wavelengths, the laser must be adjustable, and the wavelength must be scanned, which requires much time.

The CEAS method is known from the publication "Cavity Enhanced Absorption and Cavity Enhanced Magnetic Rotation Spectroscopy" by R. Engeln, G. Berden, R. Peeters, and G. Meijer in Rev. Sci. Instr. 69, 3763, dated 1998. In it, a continuous laser (cw laser) is used instead of a pulsed laser. The wavelength of the laser is continuously determined about that of the resonator over the entire spectrum. At the "correct" wavelength, the light is coupled into the resonator in a defined manner, and can thus build modes within the resonator, as with the CRDS method. If a sample that absorbs at this wavelength is located within the resonator, the reciprocally, temporally integrated, transmitted light intensity is proportional to the absorption coefficient of the sample. In other words, simple integration of the signals over time may be used to determine the concentration of the material in the sample. This method also operates only at one wavelength with narrow-band lasers. Moreover, regularly occurring mode jumps in diode lasers represent a technical disadvantage for this method. Even so-called Intra-cavity Spectrometry, in which the measurement light beam is created by a laser-active medium within the resonator, functions at only one wavelength, or is limited by the bandwidth of the laser.

A CRDS method is known from the publication "A Fourier Transform Cavity Ring Down Spectrometer" by R. Engel and G. Meijer in Rev. Sci. Instr. 67, 2708, dated 1996, in which pulsed lasers with wider bandwidth are used instead of extremely narrowband lasers. A Fourier transform spectrometer positioned after the resonator allows the required wavelength selection. The color lasers used complicate the operation of the method, and are not useable for simple or small devices. Even diode lasers are not well suited for this application because of regularly-occurring mode jumps.

Similarly, wideband, pulsed color lasers are used in the device described under the title "Pulse-Stacked Cavity Ring-Down Spectroscopy" by E. R. Crosson, P. Haar, G. A. Marcus, H. A. Schweitmann, B. A. Paldus, T. G. Spence, and N. R. Zare in Rev. Sci. Inst. 70, 4, dated 1999. The method described disperses the received laser pulses by means of a monochromator before they are received. The configuration described includes a large number of components, and is therefore expensive as well as awkward to operate because of the color lasers used.

The publication "Integrated Cavity Output Analysis of Ultra-Weak Absorption" by A. O'Keefe in Chem. Phys. Lett. 293 (1988), p. 331, describes a configuration in which a pulsed color laser is used to create the measurement light beam for CRDS whose signal is integrated with respect to time. This structure is also awkward because of the color lasers used.

A configuration is known from the publication "Fourier Transform Phase Shift Cavity Ring Down Spectroscopy" by E. Hamers, D. Schramm, and R. Engeln in Chem. Phys. Lett. 365 (2002), pp. 237-243, in which light from a Xenon arc lamp is coupled into a resonator and then the phase shift caused by the sample is measured with the help of a Fourier transform spectrometer to determine absorption. Such a configuration is expensive and susceptible to mechanical disturbance since the light intensity, for example, must be modulated by high frequency before entry into the resonator. Also, the range of spectrum that may be sampled is limited.

SUMMARY OF THE INVENTION

It is therefore the objective of the invention to provide a device of the type described above with which measurement over a large spectral range may be performed with great sensitivity. It is a further objective of the invention to provide a device that operates less expensively, more quickly, and more simply.

These objectives are achieved by the invention by providing spectrometric or interferometric means between the emission source and the detector for spectral splitting of the measurement light beam. Means may also be provided for producing a signal that represents the amplitude of the measurement light beam independently of the phase.

It has surprisingly turned out that a resonator increases the sensitivity of an absorption measurement even when an incoherent, spectrally continuous emission source is used. Spectral splitting of the measurement light beam allows particularly simple determination of the absorption coefficient at the desired wavelength. Phase-independent measurement of the amplitude does not necessarily require a complicated creation of a temporally altered intensity of the measurement light beam.

Detection of even weak transitions is possible with great sensitivity in such a configuration. Expensive lasers are no longer required. The device may be considerably more compact than with wideband color lasers because of the use of incoherent emission sources in connection with spectral splitting. This configuration allows creation of a portable device. In contrast to the DOAS applications, a very long absorption path is created with concomitant high sensitivity for the method without requiring outsize device dimensions.

An additional and significant advantage of the use of incoherent emission sources is that wideband emission over wider spectral ranges of even the visible spectrum may be simultaneously coupled into the resonator. The beams do not interfere with each other because of the super-position principle. Signals of different wavelengths may be detected simultaneously using a monochromator or polychromator. This results in considerable time savings when measurements must be made at various points of the spectrum. Spectral splitting allows simple and simultaneous measurement of a spectrum. This simplifies the evaluation and calibration, as well as impact of the configuration. Also, identification of substances in the sample is simplified, and there is the option of actually correcting undesired background during the measurement. This improves correctness of results.

Evaluation of the phase of the temporal intensity progression of the measurement light beam is not required. One may operate with an unpulsed and unmodulated source.

The means of spectral splitting is preferably a dispersing element. A dispersion grid or prism is particularly suitable. The grid may be configured as holographic or Echelle grid. Other means may be used, however, for spectral splitting, such as a Fourier transform spectrometer. Spectral splitting may be created in the wavelength range, the frequency range, the wave count range, or according to any other suitable scale. In monochromatic mode, it may scan the spectral range, or in polychromatic mode, it may receive an entire spectral range simultaneously. A horizontal or surface detector is required for this. A Charged-Coupled Device (CCD) is particularly suitable as a detector. These distinguish themselves by high sensitivity and simple operation. Any other surface detector is also suitable.

With respect to an interferometer, use of a dispersing element has the advantage that measurement may be performed simultaneously both in the visible and ultraviolet spectrum range over large wavelength ranges. These ranges contain not only rotation and oscillation transitions as in the infrared range, but also electronic transitions. Thus, much more information regarding the substance being examined is made accessible.

In a particularly advantageous embodiment of the invention, the emission source is a high-pressure Xenon short-arc lamp. Such lamps operate at a high operating pressure of up to 60 bar, and determine a spectrum of a little below 200 nm up to the near infrared range. Emission density is very high, and the emitting luminous spot of the lamps may be configured to be very small dependent on their operating condition. This allows a high-performance beam to be coupled into the resonator. Image defects that may lead to reduced beam density at the detector may be held to a low level in contrast to other lamps. The large spectral range over which the lamp emits allows measurement of a great variety of molecules. Other light sources such as Light-Emitting Diodes (LED's), halogen lamps, Deuterium lamps, simple arc lamps, and strong light bulbs are possible to the extent that they provide adequate illumination density.

In a particularly advantageous embodiment of the invention, the resonator mirrors possess great reflectivity in a selected wavelength range and very small or no reflectivity at other wavelengths. The wavelength range of high reflectivity is the measurement range, while all other light is suppressed to prevent scattered light. The reflectivity may thus possess values in the range of 99.99%. There is, however, a compromise between the sensitivity connected with high reflectivity and the signal-to-noise ratio. If reflectivity is too high, only a small portion of the measurement light beam is coupled out of the resonator for measurement. This reduces the signal. Depending on lamp quality, the reflectivity of the mirror is correspondingly selected to be more or less in order to obtain an optimum signal-to-noise ratio and to reduce the detection limits.

Further, filter media may be provided that limit the measurement light beam coupled into the resonator to the wavelength range in which the resonator mirrors possess high reflectivity. Such filters may be interference filters, red and UV filters, and combinations of these filters. The scattered light is thus reduced, and higher orders of refraction of the monochromator are prevented from falling on the detector. Wavelengths with high mirror transmission create a particularly high level of scattered light within a monochromator without such filter media.

An iris diaphragm is preferably used to reduce the beam diameter of the measurement light beam in the beam process. Using such a shutter, the edge of the measurement light beam is limited. The orders of oscillating transversal modes of the resonator are thus reduced.

Media are preferably provided to project the emission beam into the resonator. This can be a lens or a mirror. In one embodiment of the invention, media to focus the measurement light beam is provided after the resonator. In contrast to a laser light source with parallel, coherent measurement light, incoherent light sources may be strongly divergent. The beam must then be focused onto the entry slit of the monochromator or on the detector in order to obtain an optimal signal.

The detector may be configured as a horizontal or surface detector by means of which the signals of the measurement light beam may be received at several wavelengths or wavelength ranges. Simultaneous measurement also allows more information to be received, which may particularly lead to timesavings during quantitative analysis of several known substances. Also, entire absorption spectra may be received by means of which molecules may be identified. At reduced measurement times, it is also possible to identify dynamic processes with these detectors.

Evaluation of acquired absorption data that may be compiled from individual spectra of many substances may result similarly to DOAS so that the expertise thus acquired may at least partially be applied.

In another embodiment of the invention, the sample volume may be evacuated. Thus, interference from molecular nitrogen, carbon dioxide, oxygen, and other molecules present in air may be avoided, particularly during gas analysis.

The configuration may be used in the atmosphere. Because of its high degree of sensitivity, identification of weak transitions is possible. The device is particularly suited to identification of atmospheric gases and air contamination, observation of flame and combustion processes, fluids, and thin layers. Also, it may be used for long-term dependent measurements of atmospheric processes (photochemical kinetics). Measurement of absolute extinction coefficients allows expansion of databases.

For a full understanding of the present invention, reference should now be made to the following detailed description of the preferred embodiments of the invention as illustrated in the accompanying drawings.

BRIEF DESCRIPTION OF THE DRAWINGS

FIG. 3 shows two absorption spectra of the very weak $b(v=2) \leftarrow X$ transition of molecular oxygen that were obtained using different processes.

DESCRIPTION OF THE PREFERRED EMBODIMENTS

Figure 1:
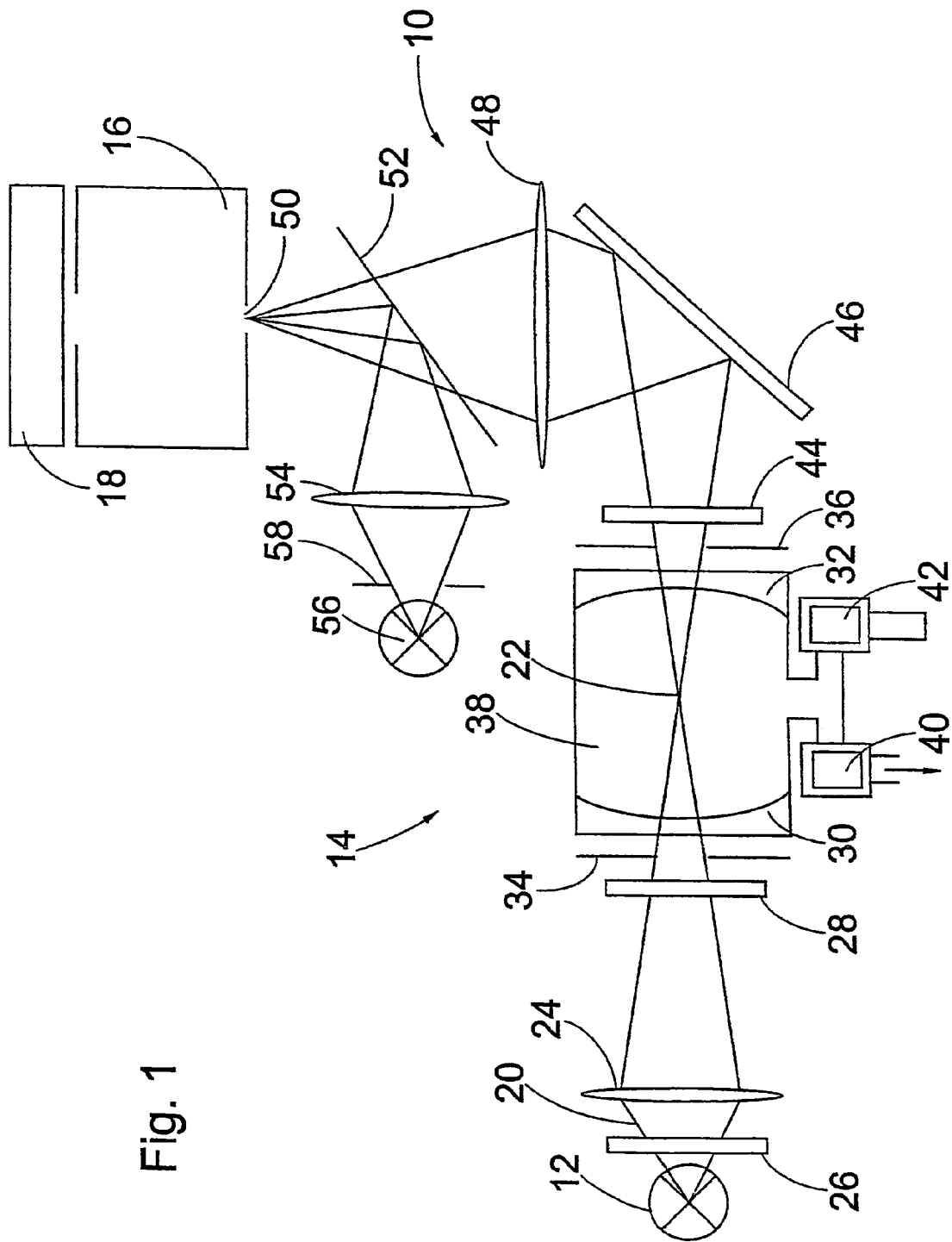
FIG. 1 is a schematic representation of a resonator-amplified absorption spectrometer.

The preferred embodiments of the present invention will now be described with reference to FIGS. 1-3 of the drawings. Identical elements in the various figures are designated with the same reference numerals.

FIG. 1 shows a wideband absorption spectrometer generally indexed with 10. The spectrometer 10 includes a high-pressure Xenon short-arc lamp 12, a resonator 14, a monochromator 16, and a detector, 18. The lamp 12 essentially consists of a glass body in which an anode is positioned above a cathode. The glass body is filled with Xenon. When voltage is applied, a conducting arc is formed between the anode and cathode. The operating pressure may increase to about 60 bar. The conducting arc emits irradiation in the wavelength range of between about 200 nm and 1200 nm. Depending on operating condition (diffuse or hot-spot), the arc is up to 150 micrometers in size. This lends to it good imaging characteristics. The lamp 12 further possesses a high spectral illumination density, i.e., high performance per unit of irradiation surface area, spatial angle, and wavelength unit. It may receive values in the range of 10-20 W/(cm$^2$ sr.nm).

The divergent beam represented by the edge beams 20 is focused on the center 22 of the resonator 14. For this, an achromatic lens 24 is used for this embodiment example. The lens 24 possesses a diameter of 15 cm and a focal length of f=11.5 cm. Using this lens, the image of the luminous spot of the lamp in the resonator is about 3 to 4 mm in size. A mirror may, of course, be used in place of the lens.

An ultraviolet (UV) filter 26 is mounted between the lamp 12 and the lens 24. The filter 26 only transmits light above 335 nm and prevents second and higher orders of refraction of the UV filter within the monochromator 16 from causing inaccurate measurement data when one is operating in the range around 610 nm.

Further, an interference filter 28 is provided before the resonator 14. The interference filter only allows beams in the range of about ±40 nm of the measurement wavelength (based on a half-width value of 40 nm) to pass. This is a part of the wavelength range for which the resonator mirrors 30 and 32 of the resonator 14 are highly reflective. All other wavelengths are suppressed. Such wavelengths at which the mirrors possess high transmission create a high level of scattered light within the monochromator. Use of the interference filter 28 reduces the level of scattered light. Depending on the wavelength range in which the measurement occurs, an interference filter with varying transmission maximum may be used.

A first iris diaphragm 34 provided between the resonator 14 and the interference filter 28. A second iris diaphragm 36 is provided after the resonator 14. The edge of the beam is cut off using the iris diaphragms 34 and 36. Thus, the order of the transversal modes of the resonator that are beginning to oscillate is reduced, and the optical quality of the beam is increased.

The resonator 14 includes two mirrors 30 and 32. These are mounted opposite each other for a selected wavelength range of about ±60 nm of the central wavelength of 610 nm in such a manner that they possess reflectivity of 99.99%. That is, 99.99% of the incident emission is reflected, and 0.01% of the emission is transmitted, discounting all other losses. The mirrors are configured as two dielectric planar-concave mirrors. They have a separation of 45 cm, and their positions are adjustable. The resonator is located within a chamber 38 capable of being evacuated. The chamber 38 may be evacuated via a first valve 40 using a pump. Further, a second valve 42 is provided by means of which a gaseous sample may be introduced into the chamber 38.

However, cuvettes or similar with a sample may be inserted into the resonator. There is then the option to silver the cuvettes themselves instead of using resonator mirrors so that their sides form the resonator.

A red filter 44 is mounted after the diaphragm 36. This serves to suppress scattered light from the long-wave range that had not already been suppressed by the interference filter.

The beam coupled out of the resonator via the mirror 32 is projected via a flat mirror 46 and a lens with a focal length f=20 cm onto the entry slit 50 of the monochromator 16. The monochromator creates a spectrum of the transmitted beam onto the detector 18 that is located in the output plane of the monochromator 16. The monochromator possesses an entry slit of 0.2 mm, a focal length of 25 cm, and a grid with 600 lines/mm. This produces a resolution of 1.2 nm in the observed wavelength range at 610 nm.

The wavelength calibration results from a Neon hollow cathode lamp 56. The irradiation from the lamp 56 may be projected for calibration via a mirror 52 and a lens 54 onto the entry slit of the monochromator. A dimmer 58 is also provided here to limit the beam path. The Neon hollow cathode lamp 56 emits a large number of very well known narrow-band lines over a wide wavelength range, and is therefore well suited for calibration. A photo-diode array is used as a detector that is coupled via glass fiber to a Micro Channel Plate (MCP) amplifier. This achieves a good signal-to-noise ratio. Evaluation of the spectra is then performed using a computer.

Figure 2:
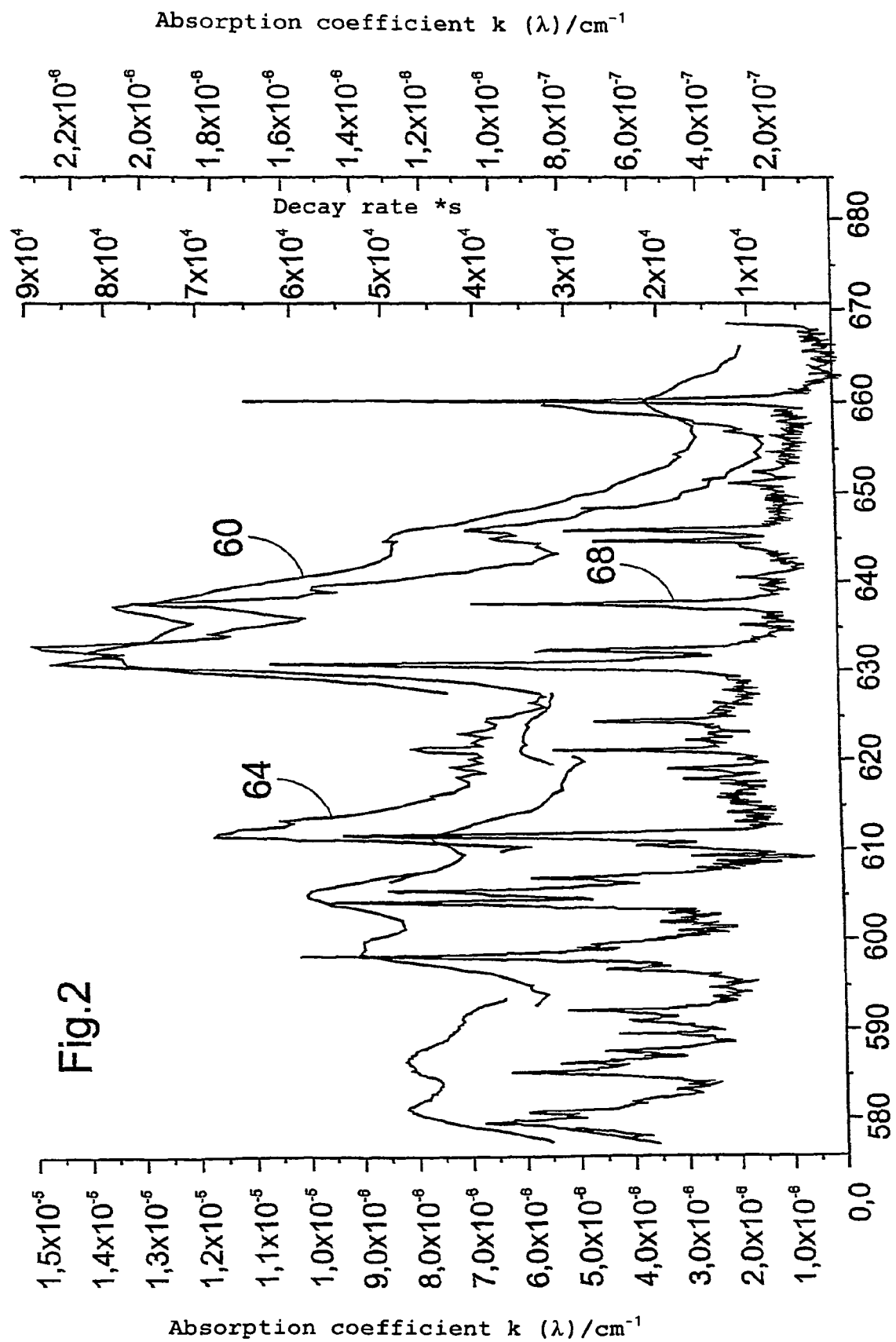
FIG. 2 shows three absorption spectra of the $S_1 \leftarrow S_0$ transition of Azuls (bluish hydrocarbon) that were obtained using different processes.

FIG. 2 shows an example 60 for an absorption spectrum of Azuls, and FIG. 3 shows an example 62 for a very weak absorption of gaseous oxygen. Spectra that were produced using CRDS and CRDS with a jet beam are shown for comparison. Spectrum 64 produced with incoherent light for Azuls, or spectrum 66 for oxygen is expanded with respect to the jet-beam CRDS spectrum 68 or 70, since the effective temperature in the jet beam is considerably less than room temperature. Pressure and Doppler broadening mechanisms thus no longer play any role. It is recognized that the spectra produced with CRDS show a progression up to an offset, as do those spectra produced with an incoherent light source.

The described configuration may be used for trace-gas analysis, for exhaust-gas inspection, and (because of the sensitivity) also for measurement of low- or zero-emission engines. Gas-Flow monitoring in vacuum evaporation facilities or measurements of atmospheric contaminants are thus also possible.

In another embodiment, the configuration is used as a detector for high-pressure fluid chromatography (HPLC). The molecules separated on the chromatographic column are investigated in a cell as in conventional absorption spectroscopy. Conventional absorption spectroscopy uses a configuration with a lamp, a cell, a monochromator, and a suitable detector. The configuration based on this embodiment also uses an optical resonator curved about the cuvette or reflective cuvette walls. The former components do not need to be exchanged. A conventional absorption spectrometer may therefore be used with very low equipment conversion costs.

There has thus been shown and described a novel resonator-amplified absorption spectrometer which fulfills all the objects and advantages sought therefor. Many changes, modifications, variations and other uses and applications of the subject invention will, however, become apparent to those skilled in the art after considering this specification and the accompanying drawings which disclose the preferred embodiments thereof. All such changes, modifications, variations and other uses and applications which do not depart from the spirit and scope of the invention are deemed to be covered by the invention, which is to be limited only by the claims which follow.

The invention claimed is:

1. Apparatus determining the absorption of a sample comprising:
   a) an incoherent-radiation source providing a measurement light beam;
   b) an optical resonator with two mirrors having planar-concave mirror surfaces arranged opposite to each other for receiving the measurement light beam, the light beam being reflected in the resonator back and forth along a path between the mirror surfaces, wherein the mirror surfaces possess a high reflectivity in a wavelength range selected for the expected measurements and a low reflectivity in all other wavelength ranges;
   c) a sample chamber within the resonator for receiving an absorbing sample;
   d) a detector for receiving radiation that is coupled out of the resonator; and
   e) means, disposed between the resonator and the detector, for spectral splitting of the measurement light beam coupled out of the resonator.

2. The apparatus defined in claim 1, wherein the means for spectral splitting include a Fourier transform spectrometer.

3. The apparatus defined in claim 1, wherein the means for spectral splitting include a dispersing element.

4. The apparatus defined in claim 3, wherein the dispersing element is a diffraction grate.

5. The apparatus defined in claim 1, wherein the incoherent radiation source comprises a high-pressure Xenon short-arc lamp.

6. The apparatus defined in claim 1, further comprising means for projecting the measurement light beam into the resonator.

7. The apparatus defined in claim 1, further comprising filter means for limiting the wavelengths of the measurement light beam coupled into the resonator to the wavelength range in which the resonator mirrors possess high reflectivity.

8. The apparatus defined in claim 1, further comprising an iris diaphragm to reduce the beam diameter of the measurement light beam.

9. The apparatus defined in claim 1, further comprising means disposed in the light path after the resonator to focus the measurement light beam.

10. The apparatus defined in claim 1, wherein the detector is at least one of a line and area detector by means of which the signals of the measurement light beam may be received at several wavelengths or wavelength ranges.

11. The apparatus defined in claim 1, wherein the sample chamber is evacuated.

12. The apparatus defined in claim 1, further comprising means for producing a signal which represents the amplitude of the measurement light beam, independent of phase.

13. A method for determining substances in samples, comprising the steps of:
  (a) providing a measurement light beam from incoherent, wideband emission;
  (b) inserting an absorbing sample into an optical resonator with two mirrors having planar-concave mirror surfaces arranged opposite to each other for receiving the measurement light beam;
  (c) coupling the measurement light beam into the resonator, the light beam being reflected in the resonator back and forth between the mirror surfaces, wherein the mirror surfaces posses a high reflectivity in a wavelength range selected for the expected measurements and a low reflectivity in other wavelength ranges;
  (d) spectrally splitting a measurement light beam coupled out of the resonator;
  (e) receiving and detecting the spectrally splitted measurement light beam; and
  (f) determining of the absorption of the sample at selected wavelengths.

14. The method defined in claim 13, further comprising the step of producing a signal which represents the amplitude of the measurement light beam, independent of phase.

15. The apparatus defined in claim 1, wherein the sample chamber is a curette of an absorption spectrometer for high-pressure fluid chromatography (HPLC).

16. The apparatus defined in claim 15, wherein the curette has reflective walls forming the resonator.

* * * * *